United States Patent [19]
Gotoh et al.

[11] Patent Number: 5,878,868
[45] Date of Patent: Mar. 9, 1999

[54] OBJECT INSPECTION APPARATUS

[75] Inventors: Kenji Gotoh; Noriyuki Ohuchi, both of Ibaraki-ken, Japan

[73] Assignee: Ikegami Tsushinki Co., Ltd., Tokyo, Japan

[21] Appl. No.: 642,895

[22] Filed: May 6, 1996

[51] Int. Cl.$^6$ .................................................. B65G 15/42
[52] U.S. Cl. ...................... 198/689.1; 198/817; 209/905
[58] Field of Search .............................. 198/688.1, 689.1, 198/817; 209/552, 559, 576, 905

[56] References Cited

U.S. PATENT DOCUMENTS

| | | | |
|---|---|---|---|
| 4,902,194 | 2/1990 | Lane | 198/689.1 X |
| 5,048,696 | 9/1991 | Evans | 209/905 X |

FOREIGN PATENT DOCUMENTS

| | | | |
|---|---|---|---|
| 6211209 | 9/1986 | Japan | 198/689.1 |
| 1-320454 | 12/1989 | Japan . | |
| 2-107383 | 4/1990 | Japan . | |
| 5-65405 | 9/1993 | Japan . | |
| 9111377 | 8/1991 | WIPO | 198/689.1 |

*Primary Examiner*—Tuan N. Nguyen
*Attorney, Agent, or Firm*—Finnegan, Henderson, Farabow, Garrett & Dunner, L.L.P.

[57] ABSTRACT

The invention relates to an apparatus for photographing and inspecting the surface of objects such as tablets. A pair of conveyor belts guided by guide rails on opposite sides of a row of suction aperture formed at even spacing in a straight line on a guide plate covering an open face of a suction box, are driven and an object seated across the pair of conveyor belts is photographed while being conveyed to thereby inspect the surface of the object. The suction apertures are formed to a size such that peripheral rims thereof are outside of the diameter of a circle having a diameter of a gap between the pair of conveyor belts on opposite sides of the suction aperture row, and the length of a portion between adjacent suction apertures is set to less than a gap between the pair of conveyor belts. Fragments of the objects being inspected are quickly sucked away from the suction apertures into the suction box, thereby preventing being caught between the conveyor belts and in the suction apertures. Moreover, even if powder of the object becomes attached to the periphery of the suction aperture, it is not photographed so that photographing inspection errors are prevented.

6 Claims, 6 Drawing Sheets

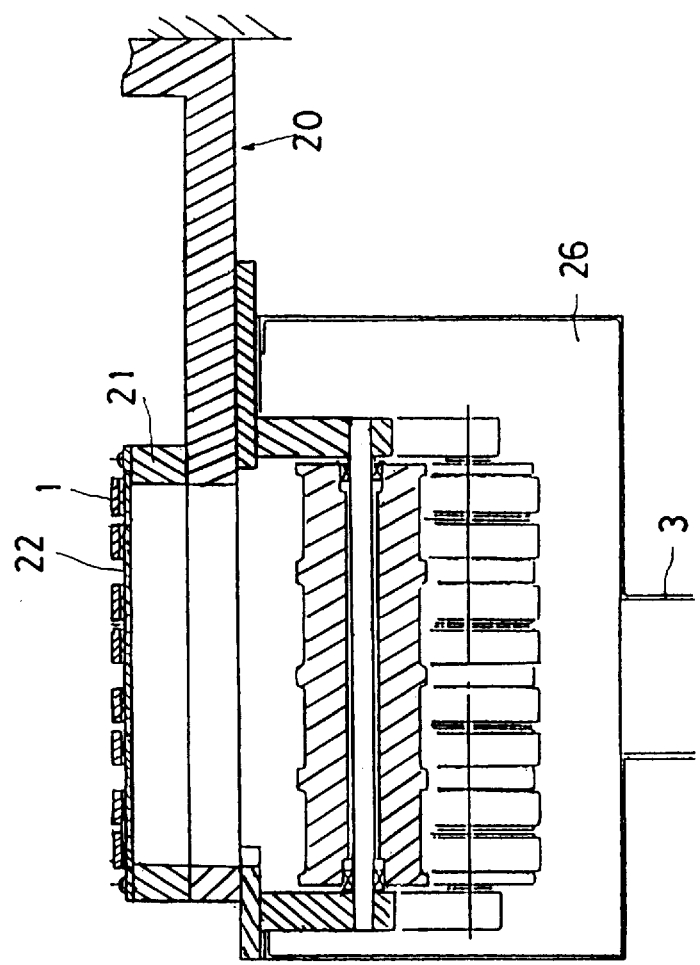

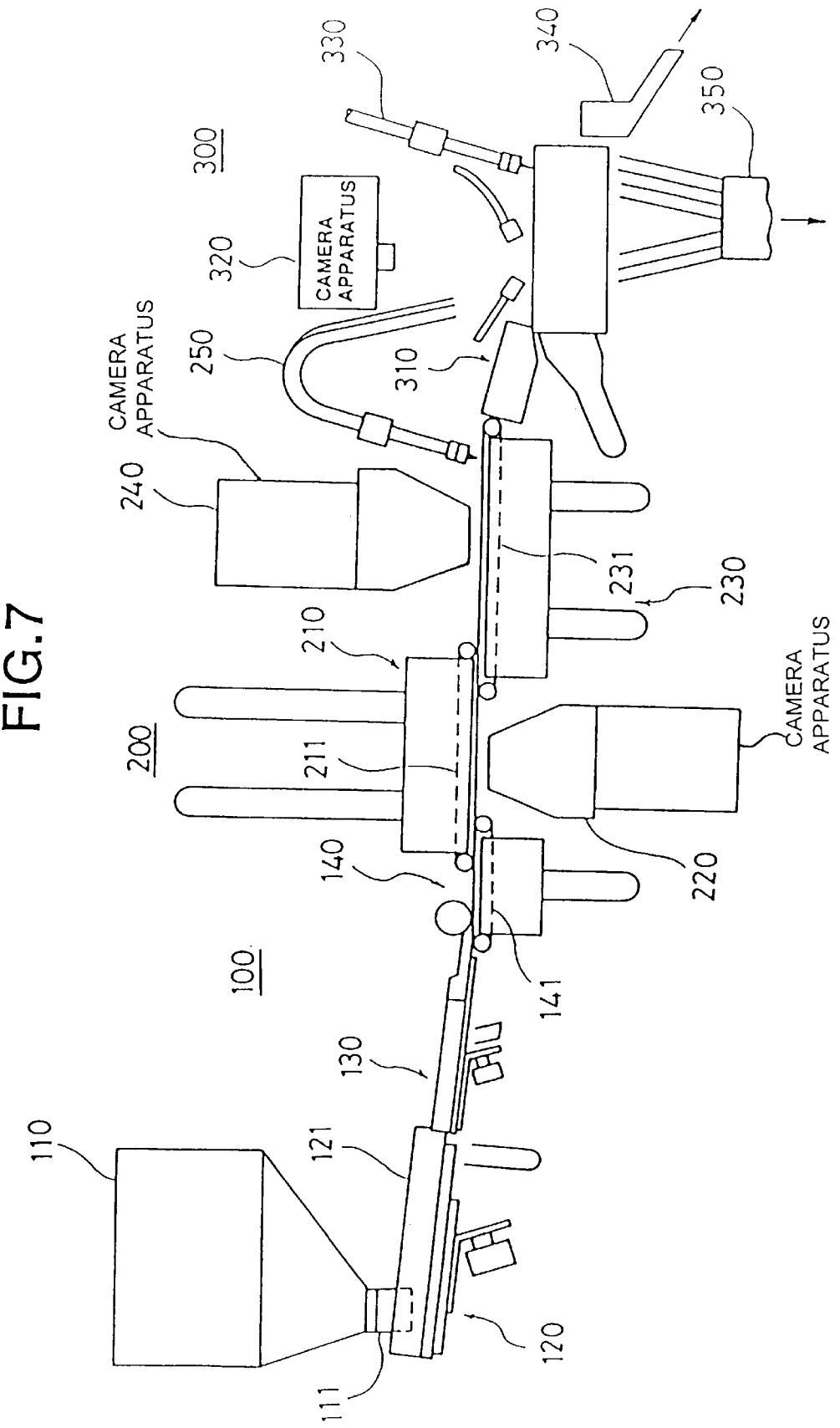

OBJECT INSPECTION APPARATUS

BACKGROUND OF THE INVENTION

(1) Field of the Invention

The present invention relates to an apparatus for inspecting for defects in small size objects such as tablets and the like, while the object is being conveyed by a conveyor.

(2) Description of the Related Art

As an example of conventional apparatus for this purpose, one of a number of various methods that have been proposed is that disclosed in Japanese Examined Patent Publication No. 5-65405. This method involves forming a slit serving as a suction opening and providing a pair of cables which are individually guided by guide rails formed on edge portions on opposite sides of the slit. Objects being inspected are placed on the cables and conveyed while being held by a negative pressure applied via the slit, and at a predetermined location the objects are photographed to thereby carry out inspection.

With such conventional arrangements however, the following various problems arise.

In practice it is difficult to form the slit by punching a single metal plate. More specifically, since the opposite sides of the slit are only bridged at the opposite ends, then even with a very rigid metal plate, it is difficult to maintain the opposite faces of the slit in the same plane, and hence a step difference in level across the slit cannot be avoided.

The slit is therefore formed for example by matching the edges of two thick very rigid plates. In this case however, extremely high manufacturing and assembly accuracy is required, incurring a significant increase in manufacturing cost merely for forming the slit. Moreover, maintenance is required to properly maintain the slit accuracy during use.

Furthermore, since normally the cables are positioned outside the slit forming the guide rails, then if a fragment from the object gets caught in the slit so as to protrude above the cables, then the objects being inspected are bumped by the fragment, the impact being sufficient to cause displacement and vibration of the objects. Hence an error occurs in the photographing inspection. Moreover, the photographing is carried out at a predetermined location, and if a fragment gets caught in the slit at the photographing location, then the fragment is photographed by the camera device so that there is the likelihood of an inspection error. Now as well as having a method wherein the object is photographed by the camera device over its whole surface, there is a method using a line sensor wherein back and forth scanning is repeatedly carried out in a straight line normal to the conveying direction, and the linearly scanned image is joined in a time series to give a surface image. With the former surface photographing method, due to the timing of the camera, when the object is photographed with a fragment lying on top, an inspection error occurs. With the latter linear scanning method, if there is a fragment lying on the scanning line, then since the fragment remains stationary, the fragment is photographed continuously, so that the resultant image of the object surface shows a streak having the same width as the fragment. There is thus the likelihood of an inspection error. Moreover, with both the surface photographing and the linear scanning method, even if a fragment gets caught away from but in the vicinity of the photographing region, then the caught fragment causes an obstruction which weakens the negative pressure applied to the object via the gap between the cables. Therefore in the case where the inspection object is a round tablet or the like, when it passes the caught fragment region, at first when the front side is above the caught fragment, the rear side is sucked with a relatively strong negative pressure so that the object inclines rearwards, then when the rear side is above the caught fragment, the front side is sucked strongly so that the object inclines forward. This results in a significant vibration so that here again inspection errors occur.

The above cases have been for when a fragment is close to the photographing location. However a problem which has a much greater probability of occurring is that with objects such as tablets, wherein fragments of the object are crushed finely into a powder which becomes attached to the inside of the slit. The occurrence of this powder is difficult to avoid with tablets and the like, and once conveying has continued for more than a certain duration the resultant quantity of powder becomes significant, evenly attaching over the whole inner wall of the slit, that is to say, also including the scanning location. In this case, with both the surface photographing method, and the linear scanning method, the powder attached to the inner wall of the slit is photographed as parallel streaks, so that there is a high possibility of considering this to be a defect in the tablet, in particular a fracture or a scratch. Hence inspection errors occur.

With the above described inspection errors due to the catching of fragments or to the attachment of powder in the vicinity of the photographing location, since these errors occur similarly for all of the objects being inspected, then once they arise practical inspection becomes impossible, and inspection is thus stopped. The fragment must then be cleared away or the powder removed, causing major problems.

In addition, the powder from the object can easily enter between the cables and the guide rails. In this case slipping of the cables can occur, and as well as being a source of inspection errors, this rubs against the cables and the guide rail faces, resulting in problems with endurance.

Now briefly considering the situation wherein the cables are fitted so that their edges protrude in from the edges of the slit forming the guide rails. In this case, since the gap between the cables is smaller than the gap of the slit, then fragments falling from the gap between the cables fall down without being caught by the slit, and fragments caught between the pair of cables are carried along as is. These can then be removed by providing a removal device such as a rotating brush downstream. Moreover, the attachment of powder to the slit wall, and the ingress of powder between the cables and the guide rails can be prevented to some degree. However in fitting the cables so that their edges protrude in from the edges of the slit, since, to ensure stable conveying, the cables must be tensioned by a certain amount so as to press against the guide rail, and since the protruding portion is subjected to the low negative suction pressure from the slit, then the same portions of the cable are continually pressed fairly hard against the edges of the slit resulting in rubbing. Therefore, there is significant deterioration and in practice from an endurance point of view this arrangement cannot be adopted.

Moreover, with slipping of the conveyor cables on the drive pulleys, a difference occurs in the conveying time from a scanning location to a sorting location where sorting is carried out based on the inspection results. Hence there is the possibility of erroneous sort.

Moreover, the slipping of the two cables can be different from each other. In this case there is the possibility of the object being rotated in a horizontal plane, resulting in a drop in the reliability of the inspection results. Alternatively, there is the situation wherein the cables rotate or twist about their axes. In this case, the object can drop into the slit so that there is the possibility of an erroneous judgement of object damage based on the inspection result.

SUMMARY OF THE INVENTION

The present invention takes into consideration the above-mentioned problems with the conventional arrangement, with the object of preventing the occurrence of inspection errors by means of a scheme for the formation and positional relationship of the suction opening and the conveying system, whereby the strength and assembly accuracy of the apparatus can be maintained, and fragments of the object being inspected can be quickly removed and thus prevented from being caught between conveyor belts, and in the suction openings.

It is a further object to prevent the occurrence of inspection errors, by improving the structure of the conveying system so that the objects being inspected are conveyed in a stable condition.

It is an even further object to prevent the occurrence of inspection errors, by designing the shape of the suction openings in combination with a scheme for the photographing position, so as to prevent the photographing of powder (from the objects being inspected) which has become attached to the suction opening.

To achieve the above objectives the object inspection apparatus according to the present invention comprises;

a suction box with a negative pressure introduced to a cavity therein by means of a negative pressure source, a guide plate attached to the suction box so as to cover an open face thereof, and including one or more suction aperture rows of a plurality of suction apertures formed at even spacing in a straight line, and provided with respective protruding guide rails on opposite sides centered on the suction aperture rows, a plurality of pulleys rotatably supported by the suction box outward from opposite end portions of the guide plate at the ends of the suction aperture rows, with one pulley rotated by a drive source, a plurality of conveyor belts in the form of loops with opposite ends of the loops engaged with the pulleys, each conveyor belt having a continuous groove for engaging with the guide rail, formed on a widthwise central portion of an inner peripheral face thereof, and a photographing section located outward from a predetermined suction aperture at a position facing objects being inspected seated across a pair of the conveyor belts while being conveyed, wherein the suction apertures are formed so that at least peripheral rims thereof are outside of the diameter of a circle concentric with the suction aperture, having a diameter of the gap between opposite side edges of the pair of conveyor belts on opposite sides of the suction aperture row, and the length of a portion between adjacent suction apertures is set to less than the gap between the opposite side edges of the pair of conveyor belts.

Describing a basic outline of the operation, the objects being inspected seated across the pair of conveyor belts on either side of the suction aperture row, are conveyed in a stable posture while being urged against the conveyor belts by the negative suction pressure introduced from the suction box via the suction apertures, and are photographed and inspected at a predetermined location by the photographing section.

As follows is a description of the characteristic individual functions of the present invention. Firstly with respect to the guide plate, due to the portion between adjacent suction apertures, the step difference which occurs when forming a slit does not occur, even if a plurality of suction apertures are provided in rows. Consequently even if a thin plate material is used for forming the guide plate, sufficient accuracy can be maintained, without the requirement for assembly accuracy.

Furthermore, since the suction apertures are larger than a circle having a diameter of the gap between the pair of conveyor belts on opposite sides of the suction aperture row, and the length of the portion between adjacent suction apertures is less than the gap between the pair of conveyor belts, then the majority of fragments from the objects which fall from the gap fall through the suction apertures into the cavity inside the suction box. Moreover even if the fragments rest on the portion between the adjacent suction apertures, since there is no securing force in contrast to the case where a fragment becomes jammed between the slit, then if hit by an object being inspected, the fragment is flicked away so that there is no influence on the inspection.

Furthermore, since the conveyor belts are supported while moving, by the portions between adjacent suction apertures, then there is minimal rubbing at the edges of the suction apertures.

With the above construction, the pulleys may be timing pulleys and the conveyor belts may be in the form of timing belts which engage with the timing pulleys.

In this case, the occurrence of slip in the conveying direction can be controlled. Moreover, transverse displacement of the conveyor belts in a direction perpendicular to the conveying direction can be controlled by engagement of the groove with the guide rail. As a result, vibration of the conveyor belts, and relative movement between the pair of conveyor belts can be controlled. Hence shaking of the inspection objects, and rotation and twisting about the horizontal due to such occurrences can be eliminated, so that inspection errors can be avoided. Moreover, since any powder attached to the conveying path surface of the guide plate is scraped out in the conveying direction by teeth of the conveyor belts, this has a good cleaning effect so that friction between the conveyor belts and the conveying path surface of the guide plate due to the powder can be prevented, resulting in excellent durability.

Moreover, the construction may be such that the conveyor belts are fitted so that portions on the opposite side of the guide plate to the guide rails, pass through the cavity inside the suction box.

With such a construction, a fragment which gets caught by the conveyor belts is carried along with the conveyor belts and is removed by suction in the suction cavity. If in addition a removal device is provided downstream of the conveying path, then the fragments can be positively and easily removed.

The construction may also be such that the photographing section carries out back and forth scanning in a predetermined cycle in a straight line passing in the vicinity of the center of the suction aperture, but not crossing a peripheral rim of the suction aperture exposed in the gap between the conveyor belts, to thereby photograph line images of the object being inspected, the line images then being connected in a time series to give a surface image.

In this way, even if powder fragments of the inspection object become attached in the vicinity of the suction aperture, since the edge of the suction aperture on the scanning line of the photographing section is hidden by the conveyor belts, then the powder will not be photographed so that inspection errors due to photographing the powder can be prevented.

Further objects and aspects of the present invention will become apparent from the following description of embodiments given in conjunction with the appended drawings.

BRIEF DESCRIPTION OF THE DRAWINGS

FIG. 6 is a longitudinal sectional view of the apparatus in a direction transverse to the object conveying direction; and FIG. 7 is an elevational view showing an outline construction of a tablet inspection system using the apparatus.

DESCRIPTION OF THE PREFERRED EMBODIMENTS

As follows is a description of an embodiment of the present invention with reference to the drawings. This embodiment is applied to an apparatus for carrying out inspection of a tablet as an object being inspected, while conveying.

Describing the basic outline with reference to FIG. 1 through FIG. 7, the apparatus comprises; a conveying apparatus comprising conveyor belts 1 in the form of loops, arranged adjacent to each other in pairs in a plurality of rows, for seating and conveying tablets (objects being inspected) supplied from a tablet supply apparatus (to be described later), and a suction box 2 with the conveyor belt 1 rows positioned on an upper portion, for applying a suction to the tablets on the conveyor belts 1 via a gap between the pair of the conveyor belts, and an inspection apparatus for photographing the surfaces of the tablets conveyed by the conveying apparatus, to thereby carry out inspection.

As follows is a detailed description of the respective parts. The respective conveyor belts 1 are made with an inner peripheral face in the form of a toothed timing belt, with a continuous groove 11 formed in a widthwise central portion.

Figure 1:
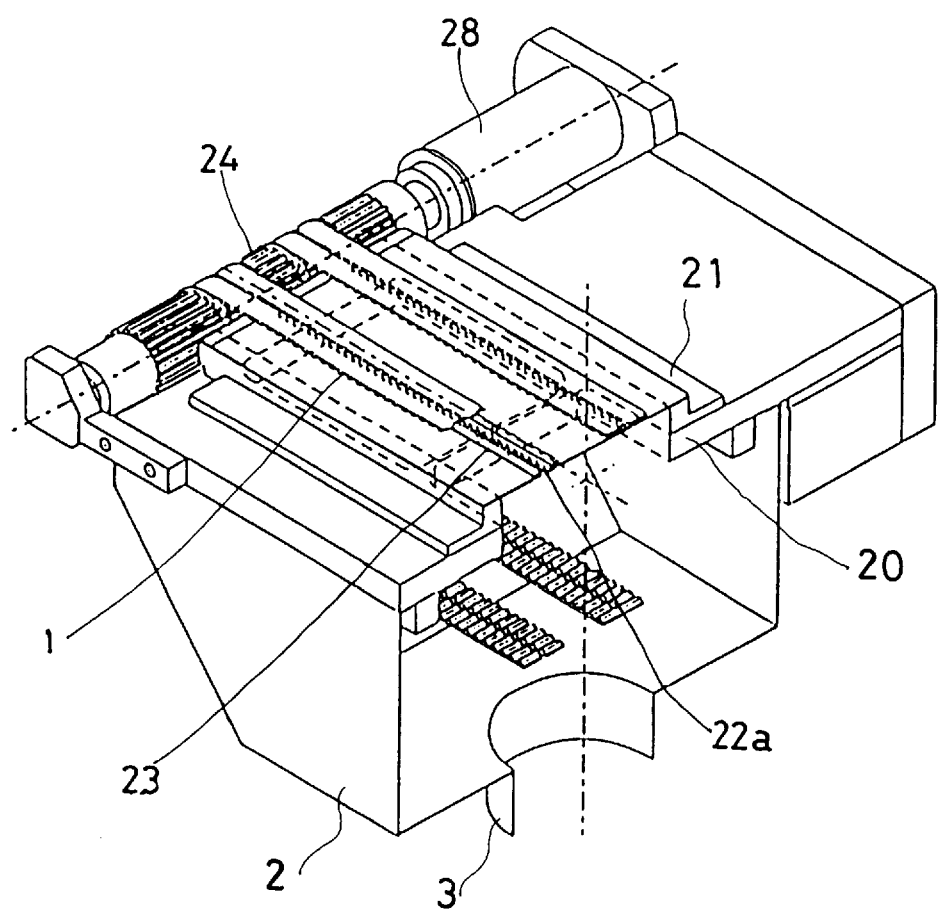
FIG. 1 is a perspective diagram showing an outline construction of an object inspection apparatus according to an embodiment of the present invention.
Figure 2:
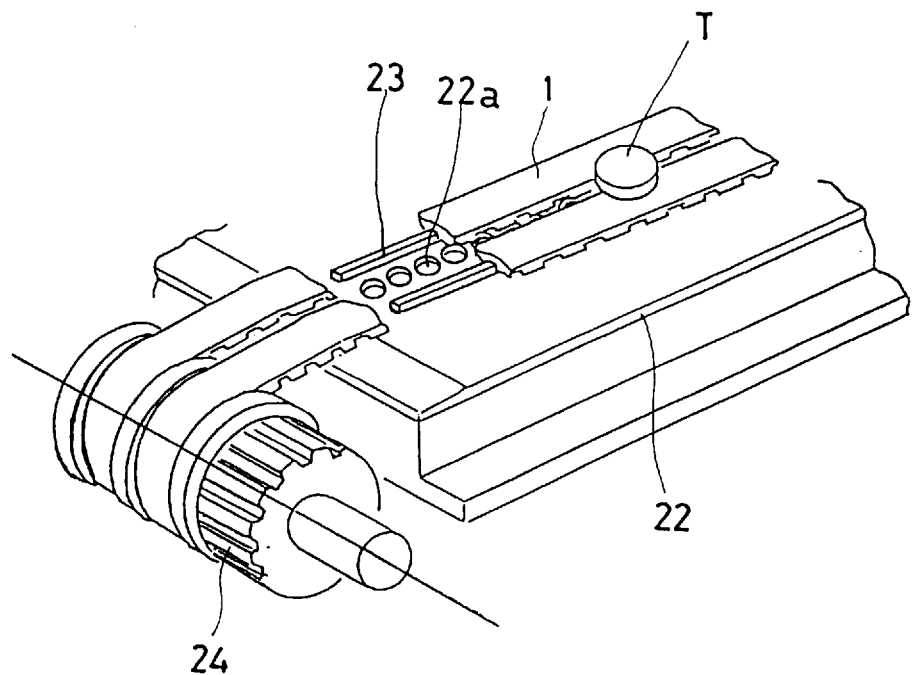
FIG. 2 is a perspective diagram of the main parts of the apparatus of FIG. 1.
Figure 3:
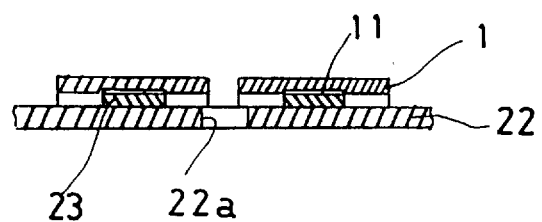
FIG. 3 is an enlarged sectional view of the main parts of the apparatus.
Figure 4:
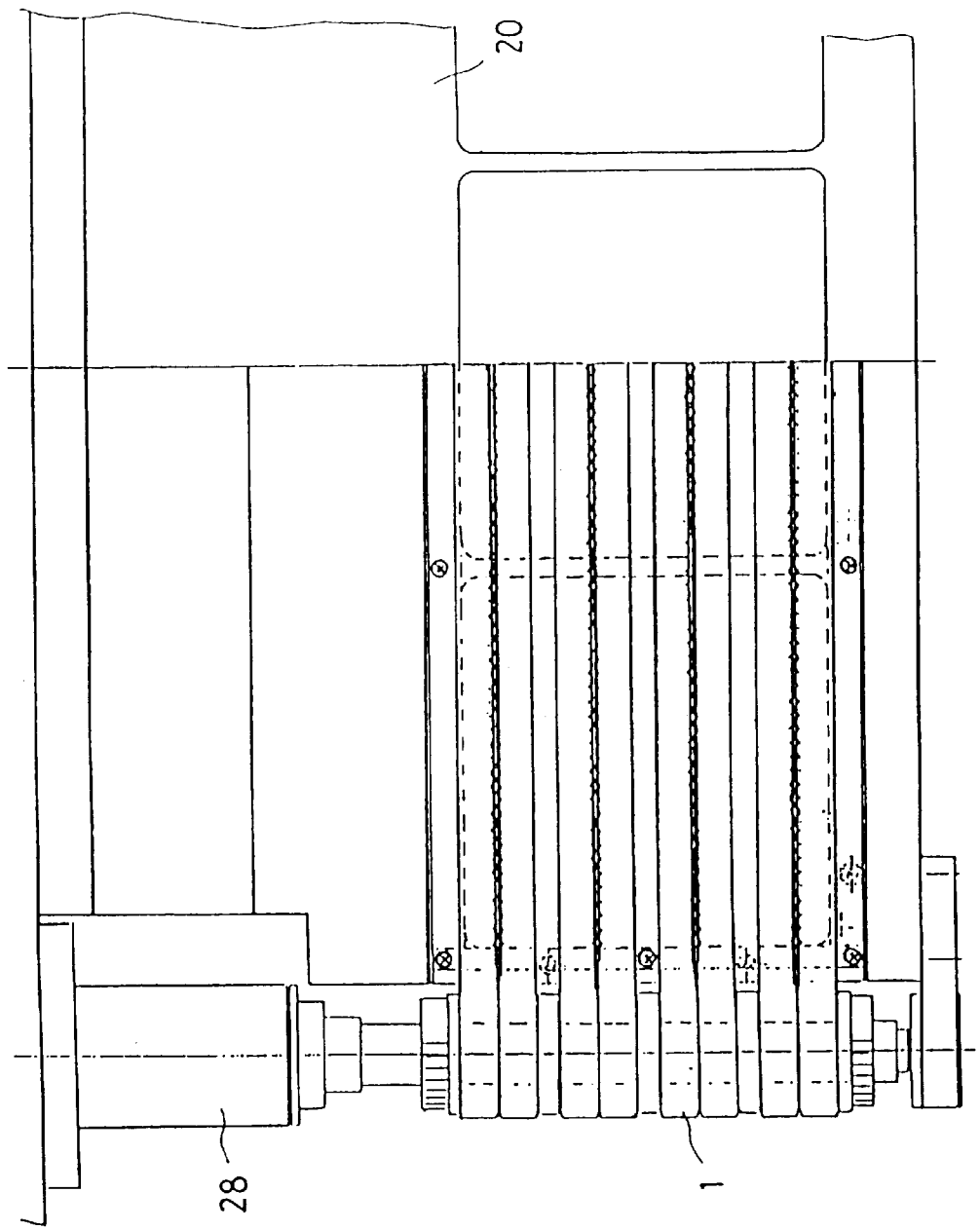
FIG. 4 is a plan view of the apparatus.
Figure 5:
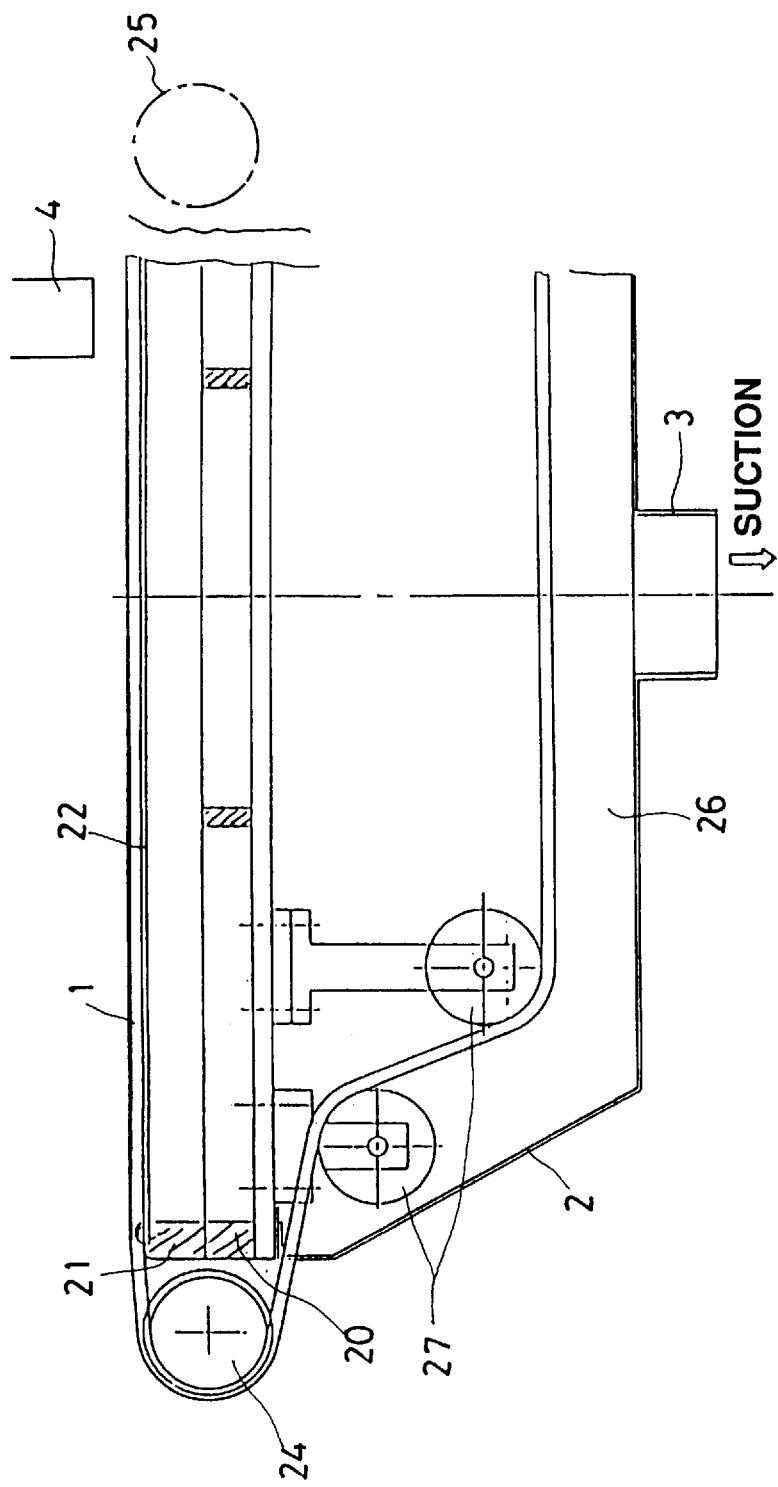
FIG. 5 is a longitudinal sectional view of the apparatus in an object conveying direction.

A solid support 20 is secured to an upper edge of the suction box 2, with a portion forming a lower side of the conveying path of the conveyor belt 1 substantially open over the whole face, except for portions at predetermined spacing in the conveying direction. A guide plate 22 is connected to the support 20 by securing opposite edge portions thereof to the upper faces of flange members 21 of an L-shape in cross-section which are secured to top outer edges of the open portion of the support 20. The guide plate 22 is provided with circular suction apertures 22a formed in a plurality of rows (with the present embodiment there are four rows, however FIGS. 1 and 2 show only one row for simplicity) by piercing the guide plate 22 at even spacing in the conveying direction. Guide rails 23 are secured to the upper face of the guide plate 22 on opposite sides of the respective suction aperture 22a rows, with the respective continuous grooves 11 of the pair of conveying belts 1 engaged therewith, to thereby guide the conveying belts 1 in the conveying direction.

Opposite ends of the conveying belts 1 are wrapped around toothed timing pulleys 24, 25 rotatably supported at opposite end portions of the suction box 2 sidewalls. The portions of the conveyor belts 1 below the timing pulleys 24, 25 pass into a suction chamber 26 inside the suction box 2, and are further wrapped around respective idler pulleys 27 inside the suction chamber 26 for applying a predetermined tension force. With this arrangement, the diameters of the suction apertures 22a are made larger than a gap between the mutually opposed inner edges of the conveyor belts 1 fitted on opposite sides of the suction aperture 22a row. Moreover, the length of the portions between adjacent suction apertures 22a is made less than the gap between the conveyor belts 1. For example, the respective ratios of the gap between the conveyor belts to the diameter of the suction apertures to the length between the suction apertures is made 2:3:1 approximately.

The end of one of the timing pulleys 24 is connected to a drive motor 28. By driving the drive motor 8, the conveyor belts 1 are driven at an even speed without slipping.

A central portion of a bottom wall of the suction box 2 is formed with an opening, and air is drawn out via a duct 3 connected thereto, by means of a vacuum pump or the like (not shown). Consequently, a negative suction pressure is applied to tablets T on the conveyor belts 1 from the suction apertures 22a via the interior of the suction box 2, so that the tablets T are conveyed on the conveyor belts 1 while being held thereagainst.

A camera apparatus 4 (photographing section) for photographing and inspecting the surface of the tablets T which have been conveyed, is provided at a predetermined location above the conveyor belts 1 of the conveying apparatus (conveyor section). The camera apparatus 4 has a one dimensional photographing element (line sensor) for photographing, which scans back and forth in a predetermined cycle in a straight line along the diameter of a predetermined suction aperture 22a, perpendicular to the conveying direction. The obtained line images are then lined up in a time series to give a surface image. Tablets found to have defects such as fractures, chips, scratches, or shape deformation, are then discharged by means of a downstream removal device (not shown). In this case, the photographing scanning line does not cross the peripheral rim of the suction aperture 22a, exposed in the gap between the conveyor belts 1.

As follows is a description of individual functions and effects of the apparatus of the embodiment.

The suction apertures 22a can be formed extremely simply by a single punching of the guide plate 22 which is made of metal or the like, and due to the portions between adjacent apertures 22a the step difference as when forming a slit does not occur. Consequently, sufficient accuracy can be maintained even if a thin metal plate is used for the guide plate 22, and since assembly accuracy is not required, manufacturing costs can be brought down significantly. Furthermore, since the accuracy after assembly can also be well maintained, then special maintenance is not required, having an added advantage for running costs.

Moreover, since the conveyor belts 1 are timing belts, then there is no occurrence of slip in the conveying direction. Also due to engagement of the continuous grooves 11 with the guide rails 23 then transverse displacement is also controlled. As a result, the occurrence of vibration of the conveyor belts 1, and the mutual approach of the pair of conveyor belts 1 due to the suction effect is prevented. Hence shaking of the tablets T, and rotation and twisting about the horizontal, due to such occurrences can be eliminated, so that inspection errors due to this can be positively prevented.

Moreover, since the diameter of the suction apertures 22a is larger than the gap between the pair of conveyor belts 1, then even if fragments of the tablet T fall from the gap, the majority will fall through the suction apertures 22a into the suction chamber 26 of the suction box 2, and even if they fall onto the portion between the adjacent suction apertures 22a, particles of a size greater than a certain amount will lose balance so that the possibility of fragments resting thereon is extremely low. Consequently, it is extremely rare in itself for fragments of a size so as to protrude above the conveyor belts 1, to rest on the portion between adjacent suction apertures 22a, and even if in a worst case scenario this does occur, then the fragment will only rest on the portion. Hence in contrast to the case where a fragment becomes jammed between the slit, since the fragment it is not secured by force, then if hit by a tablet T, it is flicked away so that there is no influence on the inspection.

Moreover, a fragment which gets caught between the conveyor belts 1 is carried along with the conveyor belt 1 and enters the suction chamber 26 where it is removed by suction. Alternatively, such fragments can be positively and easily removed by providing a rotating cleaning brush or the like downstream of the conveying path.

Next is a consideration of the situation with a powder where fragments of the tablet T are more finely crushed. In a first case where the powder becomes attached to the conveyor belt 1, since this is removed by being drawn into the suction chamber 26, or is positively removed by a rotating cleaning brush or the like, then the powder does not accumulate. Therefore inspection errors due to the powder can be simply prevented. Moreover, in a second case where the powder becomes attached in the vicinity of the suction aperture 22a, since as mentioned above, the edge of the suction aperture 22a on the scanning line of the camera apparatus is hidden by the conveyor belts 1, then any powder attached to the suction aperture 22a will not be photographed. Consequently inspection errors due to this situation can be prevented.

Furthermore, since the conveyor belts 1 are supported while moving, by the portions between adjacent suction apertures 22a, and in the case of circular shaped suction apertures 22a as with the present embodiment, there is not the situation as with a single slit wherein the same locations on the conveyor belts 1 are in continuous contact with the edge of the suction apertures 22a, then friction due to the edges of the suction apertures 22a can also be prevented.

Moreover, in the case wherein the powder of the tablet T becomes attached to the conveying path surface for the conveyor belts 1, since the powder is scraped out in the conveying direction by the teeth of the conveyor belts 1, this has a good cleaning effect so that friction between the conveyor belts 1 and the conveying path surface of the guide plate 22 due to the powder can be prevented, resulting in excellent durability.

The region above the portion of the adjacent suction apertures 22a can be considered to have a weaker negative suction pressure than the region immediately above the suction apertures 22a. However any influence due to this can be sufficiently alleviated by setting the ratio of the height of the conveyor belt 1 above the upper face of the guide plate 22 relative to the length of the portion greater than a certain amount. Moreover, since the negative suction pressure on the conveyor belt can be made sufficiently uniform due to the damping effect of the space formed between the teeth on the inner peripheral surface of the conveyor belts 1 and the guide rail 23, then the tendency to cause the tablet T to vibrate can be prevented.

FIG. 7 is a diagram showing the outline of a system, which includes equipment of the abovementioned construction, for inspecting the surface of tablets for printing and defect conditions. The system comprises a tablet array feed section 100, a two side inspection section 200, and a side face inspection section 300. The outline of the relevant inspection systems will now be described.

Tablets T contained in a hopper 110 are supplied to a conveyor belt 121 of a supply section 120 via a hopper discharge port 111. After allowing any broken pieces of tablet to be eliminated, the tablets T are supplied to an array section 130. The tablets T which have been spaced approximately evenly by means of a first conveyor belt 141 are then conveyed to the two side inspection section 200 in an upward facing posture by means of the first conveyor belt 141 of a first tablet conveying apparatus 140. The arrangement is such that even if an irregularity occurs in the spacing of the tablets T, this does not hinder the function of the two side inspection section 200.

The tablets T supplied in an upward facing posture by means of the first conveyor belt 141 are released from the suction attraction of the first conveyor belt 141 at the end thereof, and are sucked upwards at that location by means of a second conveyor belt 211 of a second tablet conveying apparatus 210. Then with the tablet T being conveyed in a downward facing posture, the rear face is photographed by a one dimensional camera apparatus 220. In this way, the tablets T are transferred from the first conveyor belt 141 to the second conveyor belt 211, and since there is only a vertical movement with the vertical switching of the suction attraction force, then as is apparent from the first embodiment, the posture of the tablet T will not be disturbed. There is thus the feature that the tablets can be transferred stably and reliably without the occurrence of tablet residue. The tablets T sucked and conveyed by the second conveyor belt 211 are transferred in a similar manner to a third conveyor belt 231 of a third tablet conveying apparatus 230, where the upper surface is photographed by a one dimensional camera apparatus 240 while the tablet T is being conveyed in an upward facing posture. Any detected faulty tablets are then selected and discharged by a discharge apparatus 250.

The tablets T which have had both sides inspected, are then sent to a side inspection section 300. Here the tablets T are changed from a flat posture to an upright posture in a posture change section 310, and inspection of the overall side face is then carried out by a one dimensional camera apparatus 320. Any faulty tablets are then selected and discharged by a discharge apparatus 330, while the fault free tablets are discharged via a discharge duct 340. The side face inspection section 300 is also provided with a tablet powder suction discharge apparatus 350.

With such an inspection system, the first and third tablet conveying apparatus 140, 230 of the first through third tablet conveying apparatus 140, 210, 230 related to the present invention, can use apparatus constructed with the conveying section of the object inspection apparatus in the embodiment shown in FIG. 1 through FIG. 6 as is, while the second tablet conveying apparatus 210 can use such an apparatus with only vertical positional relationships changed. Moreover, for the supply section 120 and the array section 130, an arrangement such as disclosed in Japanese Unexamined Patent Publication No. 2-107383 of the present applicant, for a supply section 13 and an array section 20 can be used as is, while for the side inspection section 300, an arrangement as disclosed in Japanese Unexamined Patent Publication No. 1-320454 also of the present applicant, can be used as is.

With the present invention as described above, the surface inspection of the object can be carried out with high inspection accuracy at high speed, while entirely avoiding the occurrence of inspection errors due to various possible causes. Moreover, the invention results in an apparatus having various and diverse of effects, such as enabling an apparatus of excellent durability made using low cost materials.

What is claimed is:

1. An object inspection apparatus comprising:
   a suction box for holding a negative pressure introduced to a cavity therein by means of a negative pressure source;
   a guide plate attached to said suction box so as to cover an open face thereof, said guide plate including one or more straight rows of a plurality of evenly spaced suction apertures, having opposite end portions, and having protruding guide rails on opposite sides of one or more rows;
   a plurality of pulleys rotatably supported by said suction box outwardly from the opposite end portions of said guide plate at ends of said one or more rows, one of said plurality of pulleys being rotatable by a drive source;
   a plurality of conveyor belts forming loops with opposite ends of the loops engaged with said pulleys, each of said plurality of conveyor belts having a continuous groove for engaging said guide rail, said continuous groove being formed on a transversely central portion of an inner peripheral face thereof; and
   a photographing section located outwardly over one of said suction apertures at a predetermined position facing objects being inspected and seated across said plurality of conveyor belts while being conveyed, said suction apertures having a larger diameter than a gap between mutually facing side edges of said plurality of conveyor belts over one of one or more rows, a length between adjacent ones of said suction apertures being less than said gap.

2. An object inspection apparatus according to claim 1, wherein said plurality of pulleys are timing pulleys and said plurality of conveyor belts are timing belts engaging said plurality of timing pulleys.

3. An object inspect apparatus according to either one of claim 1 and claim 2, wherein said plurality of conveyor belts are fitted such that a portion of said plurality of conveyor belts pass through inside of said suction box.

4. An object inspection apparatus according to one of claim 1 and claim 2, wherein said photographing section carries out back and forth scanning in a predetermined cycle in a straight line passing vicinity of center of said one suction aperture, said scanning not crossing a peripheral rim of said one suction aperture exposed in said gap between said plurality of conveyor belts, thereby photographing line images of the object being inspected, said line images being connectable in a time series to give a surface image.

5. An object inspection apparatus comprising:
   a suction box for holding a negative pressure introduced to a cavity therein by means of a negative pressure source;
   a guide plate attached to said suction box so as to cover an open face thereof, said guide plate including one or more straight rows of a plurality of evenly spaced suction apertures, having opposite end portions, and having protruding guide rails on opposite sides of said one or more rows;
   a plurality of pulleys rotatably supported by said suction box outwardly from the opposite end portions of said guide plate at ends of said one or more rows, one of said plurality of pulleys being rotatable by a drive source;
   a plurality of conveyor belts forming loops with opposite ends of the loops engaged with said pulleys, each of said plurality of conveyor belts having a continuous groove for engaging said guide rail, said continuous groove being formed on a transversely central portion of an inner peripheral face thereof, said plurality of conveyor belts being fitted such that a portion of said plurality of conveyer belts pass through inside of said suction box; and
   a photographing section located outwardly over one of said suction apertures at a predetermined position facing objects being inspected and seated across said plurality of conveyor belts while being conveyed, said suction apertures having a larger diameter than a gap between mutually facing side edges of said plurality of conveyor belts over one of said one or more rows, a length between adjacent ones of said suction apertures being less than said gap, said photographing section carrying out back and forth scanning in a predetermined cycle in a straight line passing vicinity of center of said one suction aperture, said scanning not crossing a peripheral rim of one of said one suction aperture exposed in said gap between said plurality of conveyor belts, thereby photographing line images of the object being inspected, said line images being connectable in a time series to give a surface image.

6. An object inspection apparatus comprising:
   a suction box for holding a negative pressure introduced to a cavity therein by means of a negative pressure source;
   a guide plate attached to said suction box so as to cover an open face thereof, said guide plate including one or more straight rows of a plurality of evenly spaced suction apertures, having opposite end portions, and having protruding guide rails on opposite sides of said one or more rows;
   a plurality of pulleys rotatably supported by said suction box outwardly from the opposite end portions of said guide plate at ends of said one or more rows, one of said plurality of pulleys being rotatable by a drive source, said plurality of pulleys being timing pulleys;
   a plurality of conveyor belts forming loops with opposite ends of the loops engaged with said pulleys, each of said plurality of conveyor belts having a continuous groove for engaging said guide rail, said continuous groove being formed on a transversely central portion of an inner peripheral face thereof, said plurality of conveyor belts being fitted such that a portion of said plurality of conveyer belts pass through inside of said suction box, said plurality of conveyor belts being timing belts engaging said plurality of timing pulleys; and
   a photographing section located outwardly over one of said suction apertures at a predetermined position facing objects being inspected and seated across said plurality of conveyor belts while being conveyed, said suction apertures having a larger diameter than a gap between mutually facing side edges of said plurality of conveyor belts over one of said one or more rows, a length between adjacent ones of said suction apertures being less than said gap, said photographing section carrying out back and forth scanning in a predetermined cycle in a straight line passing vicinity of center of said one suction aperture, said scanning not crossing a peripheral rim of said one suction aperture exposed in said gap between said plurality of conveyor belts, thereby photographing line images of the object being inspected, said line images being connectable in a time series to give a surface image.

* * * * *